US00PP30880P3

(12) United States Plant Patent
Schoone

(10) Patent No.: US PP30,880 P3
(45) Date of Patent: Sep. 10, 2019

(54) ***PHALAENOPSIS* ORCHID PLANT NAMED 'LADY LUCK'**

(50) Latin Name: *Phalaenopsis hybrida*
Varietal Denomination: Lady Luck

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 15/932,736

(22) Filed: Apr. 18, 2018

(65) Prior Publication Data

US 2018/0310452 P1 Oct. 25, 2018

Related U.S. Application Data

(60) Provisional application No. 62/487,892, filed on Apr. 20, 2017.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Annette H Para
(74) *Attorney, Agent, or Firm* — Foley & Lardner LLP

(57) ABSTRACT

A new and distinct *Phalaenopsis* plant named 'Lady Luck' particularly characterized by flowers which are purple/violet with very small white edges; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Lady Luck'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Lady Luck'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Lady Luck' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Lady Luck' originated from a cross made by the inventor in 2004 in Strengweg, Heemskerk, The Netherlands. The female or seed parent is the *Phalaenopsis* cultivar designated 'Golden Sun', unpatented. The male or pollen parent is the *Phalaenopsis* cultivar designated 'Zuma Pixie', unpatented. The new *Phalaenopsis* 'Lady Luck' was discovered and selected by the inventor as a single flowering plant within the progeny of the stated cross in a controlled environment in 2012 in Strengweg, Heemskerk, The Netherlands.

Asexual reproduction of the new *Phalaenopsis* cultivar by tissue culture (mericloning) was first performed in November, 2012 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Lady Luck', which in combination distinguish this *Phalaenopsis* as a new and distinct cultivar:

1. flowers which are purple/violet with very small white edges;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Lady Luck', the female parent 'Golden Sun' is red/purple, the male parent 'Zuma Pixie' is purple with darker purple veins and with small white edges, whereas the flowers of 'Lady Luck' are purple/violet with very small white edges.

Presently, the commercial cultivar to which 'Lady Luck' can be meaningfully compared is 'Kissy Lips'. 'Lady Luck' is purple/violet whereas 'Kissy Lips' is purple with a red/purple haze. 'Kissy Lips' is also a little smaller than 'Lady Luck'.

BRIEF DESCRIPTION OF THE PHOTOGRAPHS

The accompanying photographs illustrate the overall appearance of the new *Phalaenopsis* 'Lady Luck' showing the colors as true as is reasonably possible with colored reproductions of this type. Colors in the photographs may differ slightly from the color values cited in the detailed botanical description, which accurately describe the color of 'Lady Luck'.

DETAILED BOTANICAL DESCRIPTION

Figure 1:
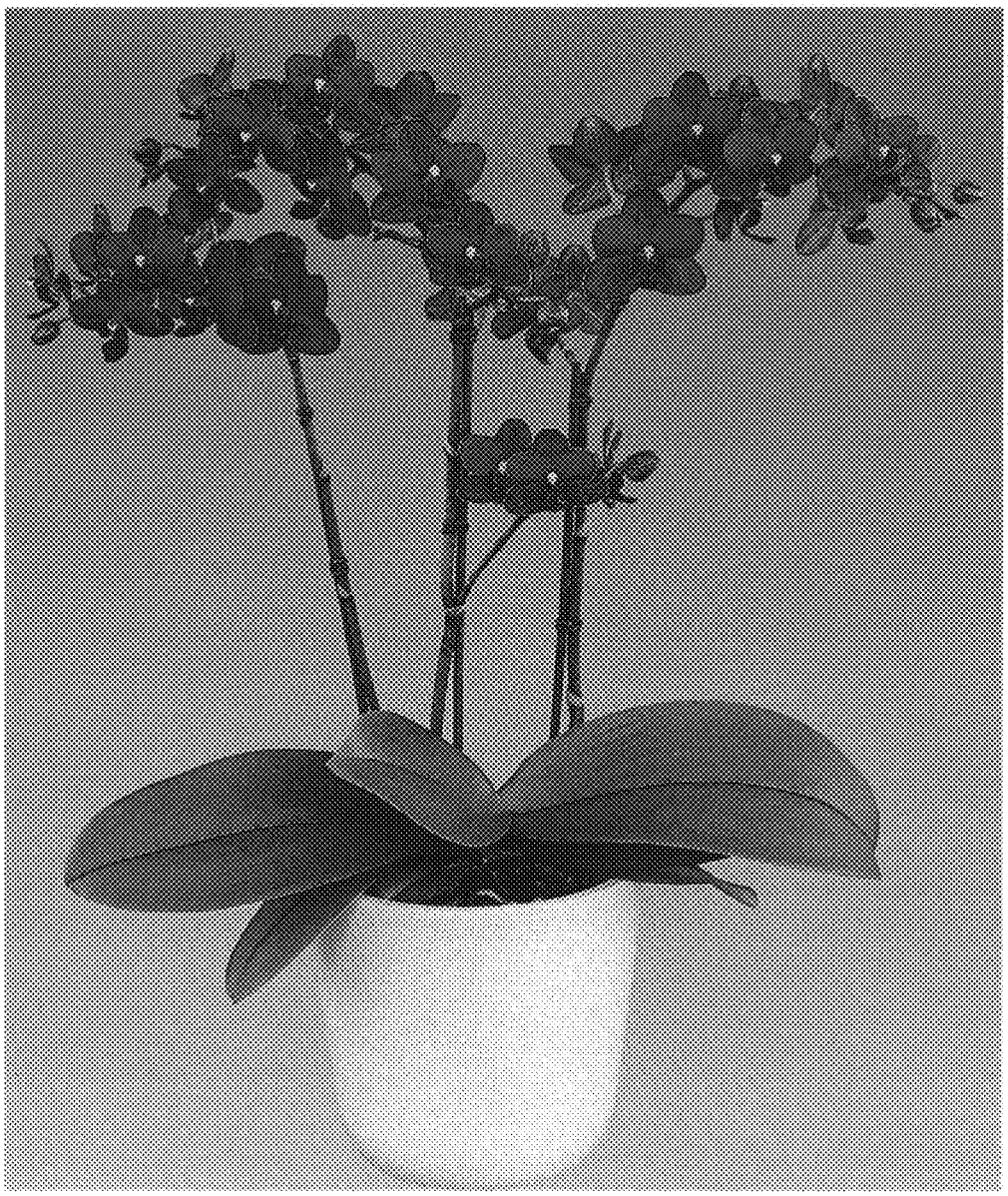
FIG. 1 shows a side view perspective of a typical flowering plant of 'Lady Luck' in a 12 cm pot, at 16 months of age.

The new *Phalaenopsis* cultivar 'Lady Luck' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Lady Luck' as grown in a greenhouse in Strengweg, Heemskerk, The Netherlands, under conditions which closely approximate those generally used in commercial practice. Initially, the ideal temperature to grow plants of 'Lady Luck' is 27° C. during the day and at night. Then, during the flowering phase of 'Lady Luck', the ideal growing temperature is 20-22° C. during the day and 18° C. at night. Light levels for growing 'Lady Luck' are a minimum of 5,000 lux and a maximum of 10,000 lux. A balanced fertilizer with level of 200 ppm N, 87 ppm P, 168 ppm K is applied. Duration of growth of 'Lady Luck' from potting size is between 10 and 14 months.

Color references are made to The Royal Horticultural Society Colour Chart (RHS), 2007 edition, except where general colors of ordinary significance are used. Color values were taken under daylight conditions at approximately noon in Zaandammerweg, Assendelft, The Netherlands. The age of the 'Lady Luck' plants described is 12 months after potting.

Classification:

*Botanical.*—*Phalaenopsis hybrida.*

Parentage:

*Female or seed parent.*—*Phalaenopsis* cultivar designated 'Golden Sun', unpatented.

*Male or pollen parent.*—*Phalaenopsis* cultivar designated 'Zuma Pixie', unpatented.

Propagation:

*Type.*—Tissue culture.

*Rooting habit and description.*—Fleshy; approximately 3 mm-5 mm wide and greyed/green in color (RHS 190A); freely branching. It takes 12 weeks for plants growing in tissue culture to initiate roots.

Plant:

*Size at maturity.*—Height (from bottom of pot to highest flower): about 55 cm Spread: about 45 cm.

*Growth habit.*—Small; green leaves (RHS 137B) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6-10 leaves are produced before flowering.

*Arrangement and attachment.*—Half up/horizontal and on two sides.

*Overall shape of leaf.*—Oval; the tip is blunt and asymmetric.

*Texture* (*upper & underside*).—Smooth and leathery.

*Pubescence.*—None.

*Mature leaf length.*—About 17 cm.

*Mature leaf width.*—About 7 cm.

*Mature leaf thickness.*—About 2 mm.

*Mature leaf color.*—Upper side: green (RHS 137B) Under side: green (RHS 137C).

*Leaf base.*—Acute.

*Margin.*—Entire.

*Venation.*—Pattern: parallel Color of midvein: upper side: green (RHS 139A) under side: green (RHS 137D).

Inflorescence description:

*Appearance.*—Upright to slightly pendant, racemose inflorescence with bilaterally symmetrical flowers that open in succession beginning with the lowermost flower.

Raceme:

*Quantity per plant.*—About 1-3.

*Number of flowers per raceme.*—About 15-20.

*Length.*—About 25 cm.

*Diameter.*—About 4 mm.

Peduncle:

*Length.*—About 20 cm.

*Diameter.*—About 3 mm.

*Strength.*—Strong.

*Aspect.*—Upright.

*Texture.*—Glabrous and smooth.

*Color.*—Green (RHS 137A).

*Buds.*—

*Height* (*from base to tip*).—About 20 mm.

*Diameter* (*at midpoint*).—About 13 mm.

*Shape.*—Asymmetric oval.

*Color.*—Purple (RHS N79A and RHS N79B) with a yellow/green haze (RHS 145C).

*Orientation.*—Same as flowers (forward facing).

*Flowering Time.*—For an untreated plant (flowering plant that has not undergone cold-treatment where the plant grows at a temperature of 18° C. to 19° C.

for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

*Flower.*—

*Rate of opening.*—Flowers fully opened about 2 to 3 days after petal and sepal separation.

*Orientation at opening.*—Slanted upward and outward.

Figure 2:
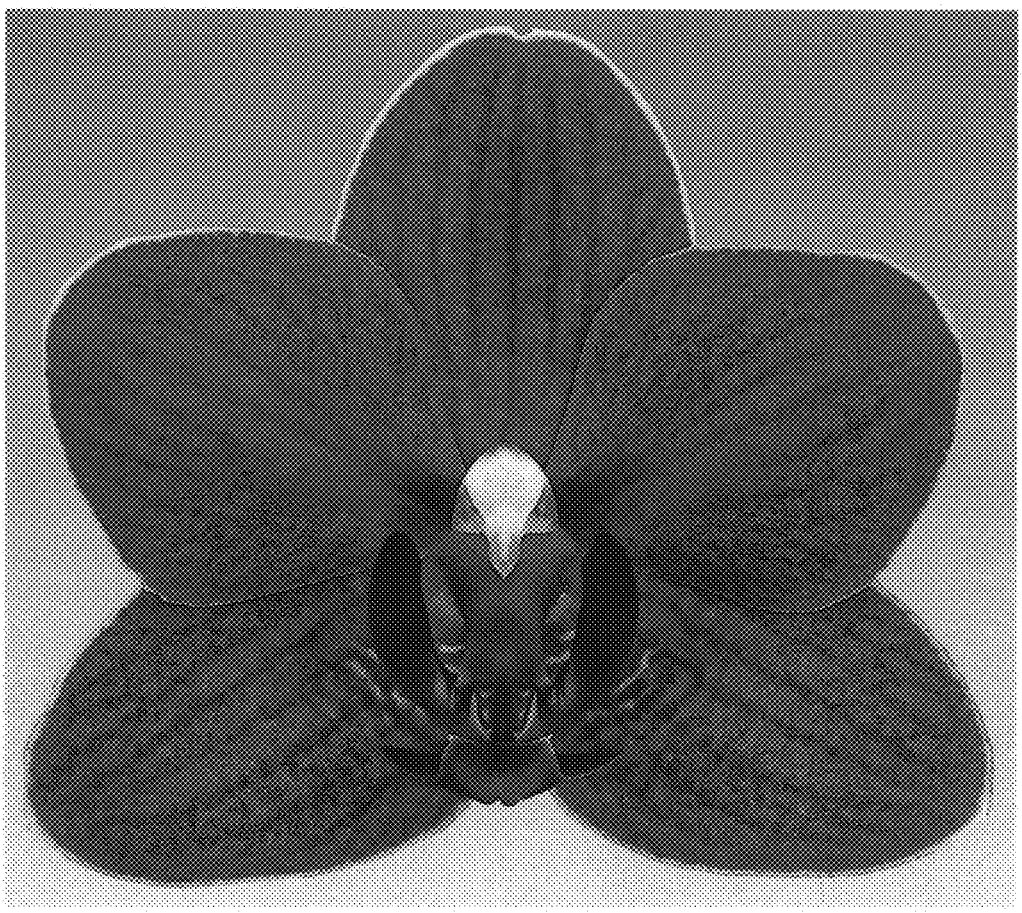
FIG. 2 shows a close-up view of the typical flower of 'Lady Luck'.
Figure 3:
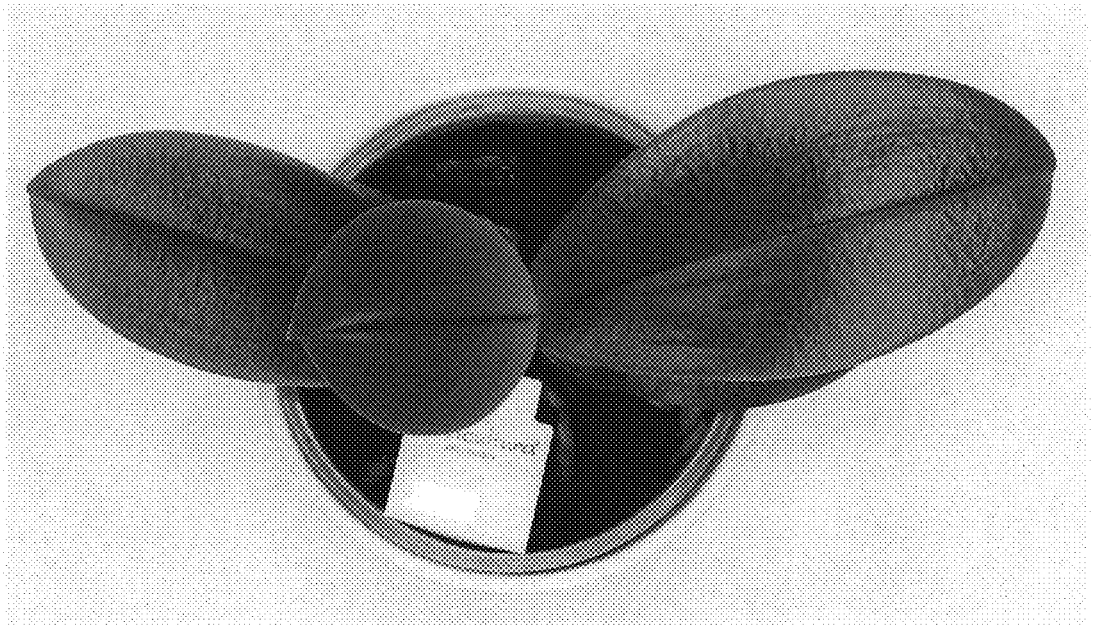
FIG. 3 shows a close-up view of the typical leaves of 'Lady Luck'.

*Shape.*—Typical shape of *Phalaenopsis*; see FIG. 2.

*Size* (*of single bloom*).—Height: about 45 mm Diameter: about 50 mm.

*Quantity and arrangement.*—Three petals and three sepals that are trimerous, overlapping and arranged in 2 whorls. Petals are more pronounced than sepals.

*Petals.*—

*Arrangement.*—Inner whorl comprises 3 petals: 2 lateral petals and a labellum.

2 *lateral petals.*—Overall shape: broadly ovate and weakly cupped Apex: round Margin: entire and weakly undulate Base: broadly ovate Length: about 20 mm Width: about 23 mm Texture: Upper surface: smooth and satiny Under surface: smooth and satiny Color (when fully opened): upper side: purple/violet (RHS N81A) with very small white edges (RHS NN155D). Under side: purple/violet (RHS N81B) with some purple/violet veins (RHS N81A) and very small white edges (RHS NN155D). Labellum: Overall shape: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin: entire and weakly undulate Apex of the midlobe and lateral lobes: oval Length midlobe: about 18 mm Width midlobe (not flattened): about 14 mm Length lateral lobe: about 12 mm Width lateral lobe (not flattened): about 5 mm Depth of tube created by lateral lobes of labellum: about 5 mm Texture: Upper & under surface: smooth and satiny Color (when fully opened): Midlobe, upper side: red/purple (RHS 59A) with purple/violet (RHS N81A) and at the end some small white edges (RHS NN155D). Under side: purple/violet (RHS N81A) with purple/violet (RHS N81C) in the center. Lateral lobes, upper side: Main color is red/purple (RHS 59A) with purple/violet (RHS N81A). At the base some yellow/orange (RHS 14B) with white (RHS NN155D). Under side: white (RHS NN155D) which runs into purple/violet and red/purple (RHS 59A). Cirrhi: about 1 mm color: purple/violet (RHS N81A) with white (RHS NN155D) Pestle (Callosities): Length: about 5 mm Width (not flattened): about 4 mm Color: yellow/orange (RHS 14A and RHS 14B) with red/purple stripes and spots (RHS 59A).

*Sepals.*—

*Arrangement.*—Outer whorl comprises 3 sepals, one dorsal and two lateral sepals.

*Overall shape.*—Elliptical and weakly cupped.

*Margin.*—Entire and weakly undulate.

*Length.*—About 27 mm.

*Width.*—About 23 mm.

*Apex.*—Oval.

*Texture.*—Upper and under surface: smooth and satiny.

*Color* (*when fully opened*).—Upper side, dorsal: purple/violet (RHS N81A) with very small white edges (RHS NN155D) and violet veins (RHS 83A). Lateral: Main color is purple/violet (RHS N81A) with violet stripes and veins (RHS 83A). At the base some white (RHS N155A) and e yellow/orange haze (RHS 14D). Also small white edges (RHS NN155D). Under side, dorsal: purple/violet (RHS N81C) with purple/violet veins (RHS N81A) and small white edges (RHS NN155D). Lateral: purple/violet (RHS N81B and N81C) with purple/violet veins (RHS N81A) and a white haze (RHS N155A) and white edges (RHS NN155D).

*Pedicel.*—

*Length.*—About 3 cm.

*Diameter.*—About 3 mm.

*Texture.*—Glabrous and smooth.

*Color.*—Red/purple (RHS 70A) with some yellow/green (RHS 145C) and a purple haze (RHS N77A).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—

*Length.*—About 13 mm.

*Diameter.*—About 4 mm.

*Color.*—Purple/violet (RHS N81A) with white at the end (RHS NN155D).

*Pollinia.*—

*Quantity.*—Two.

*Diameter.*—About 2 mm.

*Color.*—Yellow/orange (RHS 17A).

*Ovary.*—

*Length.*—About 3 mm.

*Diameter.*—About 3 mm.

*Color.*—White (RHS N155B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Lady Luck', as illustrated and described herein.

* * * * *